(12) United States Patent
Cao et al.

(10) Patent No.: US 8,835,705 B2
(45) Date of Patent: Sep. 16, 2014

(54) PRODUCTION OF PARAXYLENE

(75) Inventors: Chunshe Cao, Houston, TX (US);
Jeffrey L. Andrews, Houston, TX (US);
Michel Molinier, Houston, TX (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 93 days.

(21) Appl. No.: 13/566,311

(22) Filed: Aug. 3, 2012

(65) Prior Publication Data

US 2013/0197286 A1 Aug. 1, 2013

Related U.S. Application Data

(60) Provisional application No. 61/529,519, filed on Aug. 31, 2011.

(51) Int. Cl.
| | | |
|---|---|---|
| *C07C 4/18* | (2006.01) | |
| *C07C 5/27* | (2006.01) | |
| *B01J 29/78* | (2006.01) | |
| *B01J 29/48* | (2006.01) | |
| *B01J 37/00* | (2006.01) | |
| *B01J 35/02* | (2006.01) | |
| *B01J 37/20* | (2006.01) | |
| *B01J 29/076* | (2006.01) | |
| *B01J 29/69* | (2006.01) | |
| *B01J 37/18* | (2006.01) | |

(52) U.S. Cl.
CPC ........... *C07C 5/2708* (2013.01); *B01J 29/7892* (2013.01); *B01J 2229/42* (2013.01); *B01J 29/48* (2013.01); *B01J 37/0009* (2013.01); *B01J 2229/186* (2013.01); *B01J 37/18* (2013.01); *C07C 2529/69* (2013.01); *B01J 35/026* (2013.01); *C07C 5/2737* (2013.01); *B01J 37/20* (2013.01); *C07C 2529/48* (2013.01); *B01J 2229/36* (2013.01); *B01J 29/7853* (2013.01); *B01J 29/076* (2013.01); *C07C 4/18* (2013.01); *B01J 35/023* (2013.01); *B01J 29/69* (2013.01); *B01J 29/7861* (2013.01)
USPC ........... 585/319; 585/480; 585/481; 585/482; 585/488; 585/489

(58) Field of Classification Search
USPC .................. 585/319, 489, 488, 480, 481, 482
See application file for complete search history.

(56) References Cited

U.S. PATENT DOCUMENTS

| | | |
|---|---|---|
| 5,004,855 A | 4/1991 | Tada et al. |
| 5,028,573 A | 7/1991 | Brown et al. |
| 5,516,956 A | 5/1996 | Abichandani et al. |
| 5,763,720 A | 6/1998 | Buchanan et al. |
| 6,028,238 A | 2/2000 | Beck et al. |
| 7,271,118 B2 | 9/2007 | Raich et al. |
| 2010/0094068 A1 | 4/2010 | Levin |

FOREIGN PATENT DOCUMENTS

WO  WO 2008/033673  3/2008

*Primary Examiner* — Thuan D Dang
(74) *Attorney, Agent, or Firm* — Andrew B. Griffis; Amanda K. Jenkins

(57) ABSTRACT

The process concerns ethylbenzene conversion and xylene isomerization with a catalyst pretreated by sulfiding.

8 Claims, 5 Drawing Sheets

No start-up exotherm with presulfided catalyst

ART vs. EBC

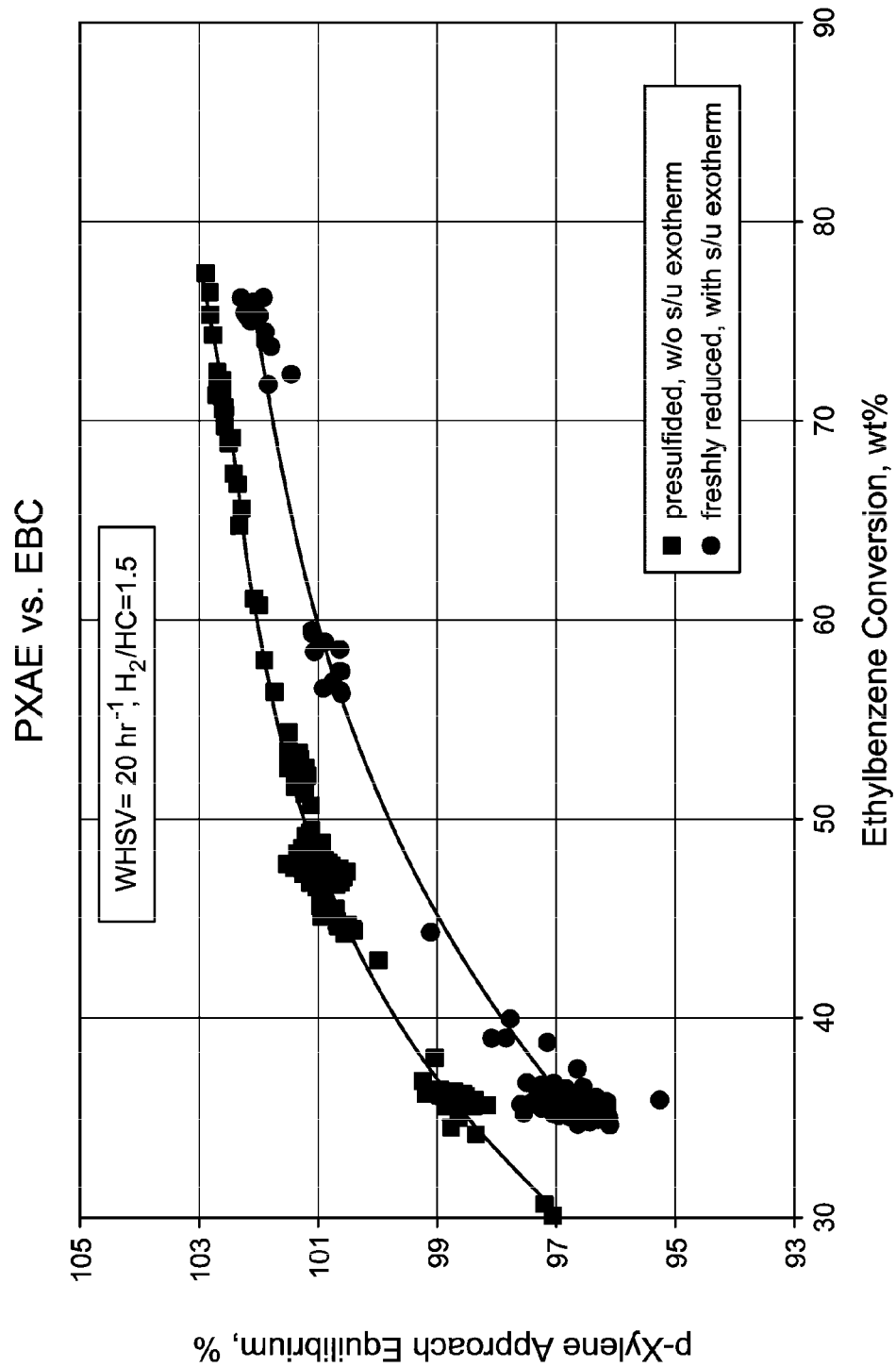

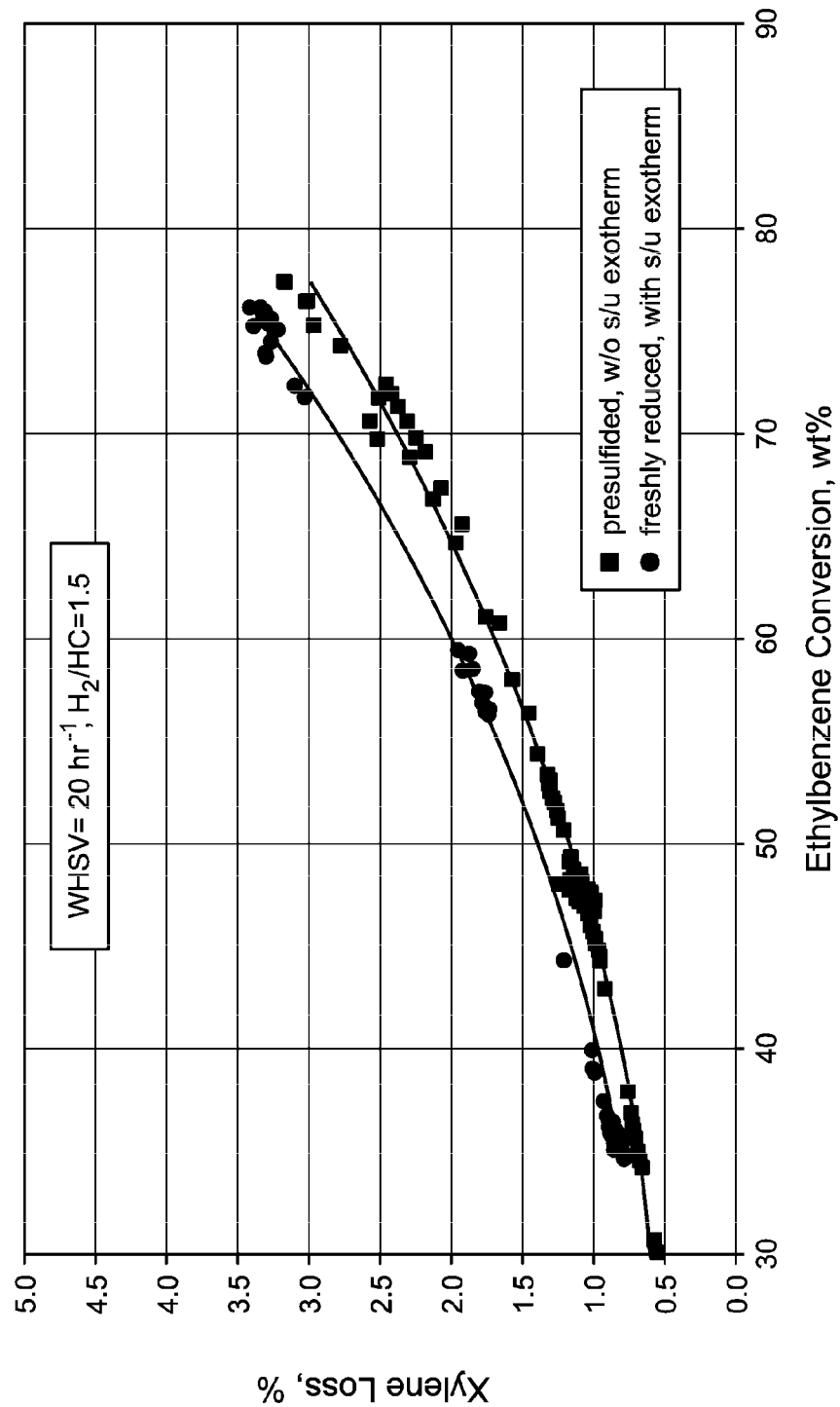

PRODUCTION OF PARAXYLENE

PRIORITY CLAIM

This application claims the benefit of Provisional Application No. 61/529,519, filed Aug. 31, 2011, the disclosure of which is incorporated by reference in its entirety.

FIELD OF THE INVENTION

The invention relates to xylene isomerization and more particularly to a method of treatment of a catalyst useful therefore and a start up procedure for a xylene isomerization process.

BACKGROUND OF THE INVENTION

Paraxylene (also "p-xylene" or "PX") is generally considered the most important of C8 aromatic isomers, being used as an intermediate or starting material for such diverse end uses as synthetic fibers and bottle plastic. Paraxylene is typically obtained from a C8 aromatic hydrocarbon mixture derived from reformate by processes including aromatic extraction and fractional distillation. Although the composition of this starting C8 aromatic hydrocarbon mixture varies over a wide range, the mixture generally comprises 5 to 40 wt % ethylbenzene, with the balance, xylenes, being divided between approximately 50 wt % meta-xylene and 25 wt % each of para-xylene and ortho-xylene (this distribution considered the nominal "equilibrium concentration" of xylenes). Since, by some accounts, 80 wt % or more of the end use of xylenes involves the conversion of para-xylene to the above-mentioned end uses, obtaining para-xylene from its C8 isomers meta-xylene, ortho-xylene, and ethylbenzene, is the subject of a vast amount of continuing research.

By way of example, U.S. Pat. No. 5,004,855 teaches a process for the conversion of ethylbenzene in an aromatic hydrocarbon mixture comprising placing a C8 aromatic hydrocarbon mixture containing ethylbenzene and xylenes in the presence of hydrogen and in contact with a catalyst comprising rhenium, an acid type of a zeolite having a main cavity inlet composed of a 10-membered oxygen ring, and alumina, said catalyst having been subjected to a sulfiding treatment, to effect conversion of ethylbenzene to benzene. In embodiments, the ethylbenzene conversion step is conducted prior to and separately from the passage of the feed through the circulation system including para-xylene separation and xylene isomerization.

In U.S. Pat. No. 5,516,956 a mixture of aromatic hydrocarbons, comprising ethylbenzene and at least one xylene, is isomerized using a two component catalyst system to convert the ethylbenzene to compounds that may be removed from the aromatic hydrocarbon stream and to produce a product stream wherein the para-xylene concentration is approximately equal to the equilibrium concentration of the para-isomer. The first catalyst comprises an intermediate pore size zeolite that is effective for ethylbenzene conversion, and the second catalyst comprises an intermediate pore size zeolite, which further has a small crystal size and which is effective to catalyze xylene isomerization. Each of the catalysts of this invention may contain one or more hydrogenation components.

In U.S. Pat. No. 6,028,238, a process is described for isomerizing a feed which contains ethylbenzene and xylene, which process comprises the steps of: (a) contacting the feed under ethylbenzene conversion conditions with a particulate first catalyst component which comprises a molecular sieve having a constraint index of 1-12, the particles of said first catalyst component having a specified surface to volume ratio and the contacting step converting ethylbenzene in the feed to form an ethylbenzene-depleted product; and then (b) contacting the ethylbenzene-depleted product under xylene isomerization conditions with a second catalyst component.

Sulfur modification of a xylene isomerization catalyst is taught in U.S. Pat. No. 7,271,118. The catalyst comprises a Group VIII metal (referring to the traditional "CAS version" of the Periodic Table).

In prior art processes such as in the above-mentioned U.S. Pat. No. 6,028,238, a paraxylene-depleted C8 aromatics feed (meaning that the amount of paraxylene is less than the equilibrium concentration referred to above) is contacted with a catalyst system that de-alkylates ethylbenzene to benzene while isomerizing the xylenes to an equilibrium mixed xylene product. The ethylbenzene dealkylation and xylene isomerization reactions are advantageously accomplished in a dual-bed catalyst system. However, in commercial practice such units often experience large start-up exotherms during the initial oil-in period (contact of the catalyst with feed). An extreme bed temperature excursion can occur particularly when the liquid feed pump is incapable of delivering the hydrocarbon flow rate to a full design capacity within a short period of time. The resulting high hydrogen to hydrocarbon ($H_2$/HC) molar ratio and high hydrogen partial pressure promote hydro-dealkylation and hydrogenolysis reactions, catalyzed by the hydrogenation metal component in the catalyst system, which in turn causes excess heat of reaction. Such a start-up exotherm can lead, among other negative consequences, to premature unit shutdown, mechanical failure of the equipment, poor isomerization performance, reduced catalyst life, and loss of xylenes, in commercial applications.

It is desirable to mitigate the start-up exotherm, so as to avoid negative consequences and maintain the high performance characteristics of the xylene isomerization catalyst.

The present inventors have surprisingly discovered a catalyst pre-treatment and start-up procedure that overcomes the disadvantages of the prior art system.

SUMMARY OF THE INVENTION

The invention concerns mitigation of large exotherms at the start-up of a process for the production of paraxylene comprising contact of a C8 aromatic hydrocarbon feed with a catalyst system, by sulfiding of the catalyst prior to contact with the feed.

In embodiments, the invention includes treating a dried and reduced catalyst comprising a hydrogenation metal so as to sulfide at least a portion of the metal. In preferred embodiments, the catalyst is treated with diluted $H_2S$ gas at an elevated temperature and pressure prior to oil-in.

It is an object of the present invention to provide a process for converting ethylbenzene to benzene and the isomerization of xylenes in a process for the production of paraxylene from a mixture of C8 aromatic hydrocarbons using a catalyst comprising a hydrogenation metal that avoids negative consequences of a high exotherm during start up procedures.

Another object of the present invention is to provide a process for the production of para-xylene including the conversion of ethylbenzene to benzene in a C8 aromatic hydrocarbon mixture with a reduced loss of xylene.

These and other objects, features, and advantages will become apparent as reference is made to the following detailed description, preferred embodiments, examples, and appended claims.

BRIEF DESCRIPTION OF THE DRAWINGS

FIG. 4 shows a performance comparison between the presulfided catalyst and the freshly reduced catalyst with respect to PX selectivity.

FIG. 5 shows a performance comparison between the presulfided catalyst and the freshly reduced catalyst with respect to xylene loss.

DETAILED DESCRIPTION

Figure 1:
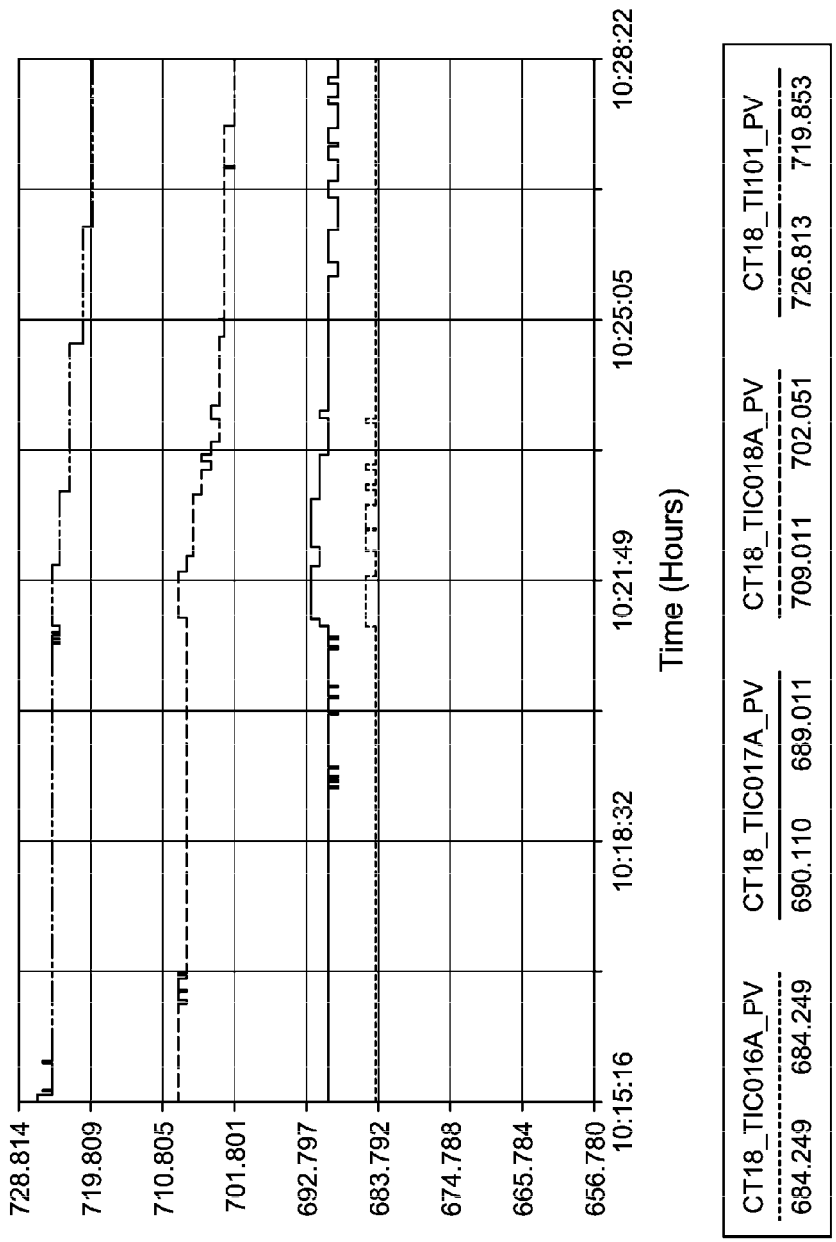
FIG. 1 is a temperature profile of the catalyst bed showing no start up exotherm using a catalyst according to the present invention.

The present invention concerns improved manufacture of paraxylene from a C8 aromatic hydrocarbon stream by a process that includes mitigation of large exotherms at the start-up of said process by sulfiding of the catalyst prior to contact with the feed ("presulfiding").

In embodiments, the method comprises treating the dried and reduced catalyst with diluted $H_2S$ gas at an elevated temperature and pressure.

Without wishing to be bound by theory, it is believed that $H_2S$ molecules are chemically adsorbed on the surface of the metal component of the isomerization catalyst to form a layer of metal sulfides. Such metal sulfides have less or no activity in aromatic ring saturation and alkane hydrogenolysis. Thus, when hydrocarbons are introduced into the reactor system, the reaction exotherm is minimized. However, the metal sulfides are not stable in the strong reducing environment following contact with the aromatic hydrocarbon feed ("on-oil"), so passivation of the catalyst metal function is of short duration and the activity suppressing or poisoning effect is reversible. Hence, the metal sulfides formed in the pretreatment step will be reduced and sulfur will desorb from the catalyst surface following aromatic hydrocarbon introduction under continuous hydrogen gas circulation at elevated temperature and pressure. Thus the long-term catalyst activity and selectivity will not be adversely affected.

The catalyst components including a hydrogenation component, such as provided by one or more metals selected from Group 7 (e.g., rhenium) or Groups 8-10 (e.g., platinum; formerly "Group VIII"), using the modern designations of the groups in the Periodic Table, a molecular sieve, and a support such as alumina or clay.

In preferred embodiments the hydrogenation component is rhenium (Re); in other embodiments the catalyst is not preselectivated such as with silica (although it may be steam-treated, as discussed in more detail below), in other embodiments the catalyst is molded by known methods known in the art per se, such as extrusion molding, compression molding, and rolling moldings. The embodiments may be combined so that, by way of example, a preferred embodiment is a catalyst comprising Re where the catalyst has not been selectivated with silica and is provided in molded form prior to sulfiding.

In general, the sulfiding used may be any method capable of converting the hydrogenation component to a sulfide in a current of hydrogen sulfide at from above room temperature to 540° C., preferably 100° C. to 450° C. The time of the sulfiding treatment is not particularly critical, however, the treatment should be conducted after the hydrogenation component has been supported on the catalyst, methods of which are per se known in the art. Preferred methods of applying said component to the catalyst include impregnation, ion exchange, or mixing.

In general, the feedstock may comprise an aromatic C8 mixture containing ethylbenzene and at least one xylene isomer and typically all three of the xylene isomers. In embodiments the feedstream will be para-xylene depleted, meaning that the concentration of para-xylene in the feedstream, relative to its C8 isomers, will be lower than the thermodynamic equilibrium concentration of para-xylene in a mixture of C8 isomers. In embodiments the feedstream will have an ethylbenzene content in the approximate range of 5 to 60 wt %, an ortho-xylene content in the approximate range of 0 to 35 wt %, a meta-xylene content in the approximate range of 20 to 95 wt % and a para-xylene range of 0 to 15 wt %.

In addition, the feedstream comprising C8 aromatic hydrocarbons may contain non-aromatic hydrocarbons, e.g., naphthenes and paraffins, such as in an amount up to 30 wt %.

In a preferred embodiment, the invention provides a method to process a starting mixture comprising C8 aromatic hydrocarbons, such as that derived from catalytic reforming of a petroleum naphtha, to obtain a product mixture of C8 aromatic hydrocarbons having a reduced ethylbenzene content and increased paraxylene content relative to said starting mixture, said method having at least one advantage selected from longer catalyst life, longer on-oil time, reduced xylene loss, and increased paraxylene recovery. The invention is particularly effective in treating a paraxylene lean mixture of C8 aromatic hydrocarbons to increase the paraxylene concentration up to approximately the thermal equilibrium level.

The process of the present invention is especially suitable for the isomerization of C8 aromatic hydrocarbon streams that contain about 5 to 60 wt % ethylbenzene, e.g., about 8 to 15 wt % ethylbenzene. This range spans the range of ethylbenzene concentrations of streams that are derived from a reformer and a pyrolysis gasoline unit. In certain embodiments, the presulfided catalyst of the present invention is believed to have the advantage of high activity for cracking of normal and branched paraffins of the type present in unextracted C8 aromatic streams.

The catalyst system of the invention includes at least two catalyst components, the first of which has the primary function of selectively de-ethylating the ethylbenzene in the feedstream to benzene, while the second catalyst component selectively isomerizes xylenes in the feed. The first catalyst component can, and preferably will, effect some isomerization of the xylenes in the feed. Such catalyst systems and the respective components are per se known in the art and can be selected by one of ordinary skill in the art in possession of the present disclosure. Particularly preferred systems are disclosed, for instance, in the aforementioned U.S. Pat. Nos. 5,516,956 and 6,028,238, mindful of the teachings of the present disclosure.

In embodiments, each of the first and second catalyst components comprises an intermediate pore size molecular sieve which is characterized by a Constraint Index within the approximate range of 1 to 12 (e.g., less than about 7 Angstroms pore size, such as from about 5 to less than about 7 Angstroms). The term "Constraint Index" is well-known in the art. The method by which Constraint Index is determined is described fully in U.S. Pat. No. 4,016,218, incorporated herein by reference for details of the method. Examples of intermediate pore size molecular sieves useful in this invention include ZSM-5 (U.S. Pat. Nos. 3,702,886 and Re. 29,948); ZSM-11 (U.S. Pat. No. 3,709,979); ZSM-12 (U.S. Pat. No. 3,832,449, ZSM-22 (U.S. Pat. No. 4,556,477); ZSM-23 (U.S. Pat. No. 4,076,842); ZSM-35 (U.S. Pat. No. 4,016, 245); ZSM-38 (U.S. Pat. No. 4,406,859); ZSM-48 (U.S. Pat. No. 4,397,827); ZSM-57 (U.S. Pat. No. 4,046,685); and ZSM-58 (U.S. Pat. No. 4,417,780).

The molecular sieve of each of the first and second catalyst components is also associated with at least one hydrogenation component. Examples of such components include the oxide, hydroxide, sulfide, or free metal (i.e., zero valent) forms of the metals discussed above (i.e., selected from Groups 7-10) and also from Group 6 (i.e., Cr, Mo, W), Group 11 (i.e., Cu, Ag, Au), Group 14 (i.e., Sn and Pb), and Group 15 (i.e., Sb and Bi). Combinations of catalytic forms of such noble or non-noble metal, such as combinations of Pt with Sn, may be used. The metal is preferably in a reduced valence state, e.g. when this component is in the form of an oxide or hydroxide. The reduced valence state of this metal may be attained by methods per se known in the art, e.g., in situ, such as when a reducing agent, e.g., hydrogen, is included in the feed to the reaction. In preferred embodiments the metal is rhenium and it is present in the reduced state in the dried catalyst prior to sulfiding.

As far as incorporation of the hydrogenation component into the catalyst, it is preferred that said component be incorporated into the catalyst by ion exchange, impregnation or physical admixture. For example, solutions of appropriate metal salts may be contacted with the remaining catalyst components (molecular sieve and support such as alumina and/or clay), which have preferably not been selectivated with silica, under conditions sufficient to combine the respective components. The metal containing salt is preferably water soluble. Examples of suitable salts include perrhenic acid (HReO4). Suitable methods of preparation also include the use of aqueous solutions of rhenium oxides, such as disclosed in U.S. Pat. No. 5,004,855. After incorporation of the metal, the catalyst can then be filtered, washed with water and calcined at temperatures of from about 250 to about 500° C. In embodiments the thus-prepared dried and calcined catalyst is then loaded in a reactor, dried, and then reduced, such as under flowing hydrogen, prior to sulfiding.

The amount of the hydrogenation component is suitably from about 0.001 to about 10 percent by weight, e.g., from about 0.1 to about 5 percent by weight, e.g., from about 0.1 to about 2 percent by weight, although this will, of course, vary with the nature of the component and other factors, as would be appreciated as well as optimized by one of skill in the art in possession of the present disclosure.

The above-described preparation of the dried and calcined catalyst, comprising molecular sieve, hydrogenation component, and optional support such as by alumina and/or clay, does not form a necessary part of the present invention per se and is within the skill of the ordinary artisan to prepare by no more than routine experimentation.

In practicing the process of the invention, it may be desirable to formulate either or both of the first and second catalyst components with another material resistant to the temperature and other conditions of the process, e.g., a support or matrix. Such matrix materials include synthetic or naturally occurring substances as well as inorganic materials such as clay, silica, and/or metal oxides. The metal oxides may be naturally occurring or in the form of gelatinous precipitates or gels including mixtures of silica and metal oxides. Naturally occurring clays which can be composited with the molecular sieve include those of the montmorillonite and kaolin families, which families include the subbentonites and the kaolins commonly known as Dixie, McNamee, Georgia and Florida clays or others in which the main mineral constituent is halloysite, kaolinite, dickite, nacrite or anauxite. Such clays can be used in the raw state as originally mined or initially subjected to calcination, acid treatment or chemical modification.

In addition to the foregoing materials, the molecular sieves employed herein may be composited with a porous matrix material, such as alumina, silica-alumina, silica-magnesia, silica-zirconia, silica-thoria, silica-berylia, silica-titania, as well as ternary compounds such as silica-alumina-thoria, silica-alumina-zirconia, silica-alumina-magnesia, and silica-magnesia-zirconia. A mixture of these components could also be used. The matrix may be in the form of a cogel. The relative proportions of molecular sieve component and inorganic oxide gel matrix on an anhydrous basis may vary widely with the molecular sieve content ranging, in embodiments, from between about 1 to about 99 percent by weight and more usually in the range of about 10 to about 80 percent by weight of the dry composite.

The first and second components of the catalyst system of the invention should be selected so that the respective components differ from each other in a number of significant respects which ensure that first component selectively deethylates the ethylbenzene in the feedstream to benzene while the second component selectively isomerizes xylenes in the feed. While selection of details of the catalyst to be sulfided are within the skill of the ordinary artisan in possession of the present disclosure, certain preferred characteristics are discussed below.

In embodiments, the first and second components of the catalyst system of the invention differ in their particulate form and size. The first catalyst component is preferably composed of particles having a surface to volume ratio of about 80 to about 200 $inch^{-1}$, whereas the second catalyst component will typically be composed of particles with a surface to volume ratio less than 80 $inch^{-1}$.

Ethylbenzene Conversion Component: according to embodiments of the invention, the first catalyst component, which selectively deethylates the ethylbenzene in the feedstream to benzene, is selected so as to have a surface to volume ratio of about 80 to <200 $inch^{-1}$, preferably about 100 to 150 $inch^{-1}$. It has been found that the ethylbenzene conversion reaction is sensitive to intraparticle (macroporous) diffusion limitations. By selecting the shape and size of the particles of the first catalyst component such that the surface to volume ratio is within the specified range, it is found that the intraparticle diffusion distance can be decreased without excessively increasing the pressure drop across the first catalyst bed. As a result, the xylene losses accompanying the ethylbenzene conversion in the first catalyst bed can be reduced, while at the same time the xylene isomerization activity of the first catalyst component can be increased. Producing a first catalyst component with the desired surface to volume ratio can readily be achieved by controlling the particle size of the catalyst or by using a shaped catalyst particle, such as the grooved cylindrical extrudate described in U.S. Pat. No. 4,328,130 or a hollow or solid polylobal extrudate as described in U.S. Pat. No. 4,441,990, the entire contents of both of which are incorporated herein by reference. For example, a cylindrical catalyst particle having a diameter of 1/32 inch and a length of 3/32 inch has a surface to volume ratio of 141, whereas a quadralobed solid extrudate having the external shape disclosed in FIG. 4 of U.S. Pat. No. 4,441,990 and having a maximum cross-sectional dimension of 1/16 inch and a length of 3/16 inch has a surface to volume ratio of 128. A hollow tubular extrudate having an external diameter of 1/10 inch, an internal diameter of 1/30 inch and a length of 3/10 inch has a surface to volume ratio of 136.

In embodiments, the first catalyst component preferably has enhanced macroporosity which is achieved by adding a thermally decomposible organic material to the mix used to extrude the catalyst particles; and then calcining the extruded particles to remove the organic material. The thermally decomposible organic material can be any material which is compatible with the extrudable mix used to form the catalyst particles and which is retained within the mass of the extruded catalyst particles but which can be removed from the catalyst particles by heating to leave macroporous voids within the particles. A suitable organic material is a cellulose such as that sold under the trade name Avicel.

In embodiments, the molecular sieve of the first catalyst component preferably has a higher acid activity (and thus a higher alpha value) than the molecular sieve of the second catalyst component. Thus molecular sieve of the first catalyst component preferably has an alpha value of at least 50 and typically has an alpha value of about 100 to about 500. Most preferably, the alpha value of the molecular sieve of the first catalyst component is between 100 and 300. The alpha test is described in U.S. Pat. No. 3,354,078; in the Journal of Catalysis, Vol. 4, p. 527 (1965); Vol. 6, p. 278 (1966); and Vol. 61, p. 395 (1980), each incorporated herein by reference as to that description. The experimental conditions of the test used herein include a constant temperature of 538° C. and a variable flow rate as described in detail in the Journal of Catalysis, Vol. 61, p. 395. The higher alpha values correspond with a more active cracking catalyst. Modification of the catalyst acidity can be achieved by contacting the catalyst with high temperature steam. The desired level of acidity (alpha values) can be achieved by controlling steaming temperature and duration, in a manner well-known to one of ordinary skill in the art.

In embodiments, each of the components of the catalyst system of the invention will normally exhibit mutually exclusive xylene diffusional properties. These properties can be identified by noting the time (in minutes) required to sorb 30% of the equilibrium capacity of ortho-xylene at 120° C. and at an ortho-xylene partial pressure of 4.5+−0.8 mm of mercury, a test described in U.S. Pat. Nos. 4,117,026; 4,159,282; and Re. 31,782. The equilibrium capacity of ortho-xylene is defined herein as greater than 1 gram of xylene(s) per 100 grams of molecular sieve. In the catalyst system of the invention, the first catalyst component effective for ethylbenzene conversion preferably has an ortho-xylene sorption time (in minutes) in excess of about 50 and preferably greater than about 1200, but less than 10,000 minutes, while on the other hand, the second, isomerization component preferably has an ortho-xylene sorption time of less than about 50 minutes and preferably less than about 10 minutes.

In embodiments, the xylene diffusion properties of the first catalyst component is achieved in a number of ways. For ortho-xylene diffusion times at or near the minimum value of 50 minutes, the selection of a large crystal form of the molecular sieve used in the catalyst, that is having an average crystal size in excess of 1 micron, may be sufficient.

The second component of the catalyst system is effective to isomerize the xylenes of the feed containing C8 aromatics. The second, isomerization component preferably has an ortho-xylene sorption time of less than about 50 minutes and preferably less than about 10 minutes. This is typically achieved by using a small crystal size molecular sieve, having an average crystal size of 0.02-0.05 micron, in this component. The molecular sieve of the second component of the catalyst system will typically have an alpha value less than about less than 50 and preferably from about 5 to about 25. The second component of the catalyst system may be prepared with the use of a thermally decomposible organic material so as to increase its macroporosity. In addition, the size and shape of the particles of the second catalyst component can be selected so as to have a surface to volume ratio of about 80 to <200 inch$^{-1}$, preferably about 100 to 150 inch$^{-1}$.

After preparation as set forth above, the catalyst is sulfided in accordance with the present invention. Preferably the catalyst is sulfided in situ. In embodiments, the treatment comprises flowing hydrogen which contains 100-600 vppm $H_2S$ gas at elevated temperature such as from above room temperature to about 500° C., preferably 100° C. to 450° C. Normally liquid DMDS (dimethyl disulfide) is used as sulfiding agent. DMDS decomposes to $H_2S$ and methane once entering the reactor. The extent of sulfiding is preferably selected to obtain 0.5 to 3.0 equivalents of catalyst metal content.

Conditions such as WHSV and $H_2$:HC at initial oil-in can be determined by one of ordinary skill in the art in possession of the present disclosure without more than routine experimentation. In this regard, it is useful to keep in mind that in a commercial plant, typically the liquid feed pump is incapable of delivering the hydrocarbon flow rate to a full design capacity within a short period of time. This results in low WHSV and high hydrogen to hydrocarbon molar ratio and high hydrogen partial pressure, which promote hydro-dealkylation and hydrogenolysis reactions catalyzed by hydrogenation component such as Re, leading to excess heat of reaction.

When the presulfided catalyst system according to the present invention is contacted with the feedstream, the conditions used in the process of the invention are not narrowly defined, but generally will include a temperature of from about 400 to about 1,000° F. (about 204° C. to about 537° C.), a pressure of from about 0 to about 1,000 psig (6.895 MPa-g), a weight hourly space velocity (WHSV) of between about 0.1 and about 200 hr$^{-1}$, and a hydrogen, $H_2$, to hydrocarbon, HC, molar ratio of between about 0.2 and about 10. Preferably, the conditions include a temperature of from about 650 to about 850° F. (about 340-450° C.), a pressure of from about 50 and about 400 psig (about 0.34 to 2.76 MPa-g), a WHSV of between about 3 and about 50 hr$^{-1}$ and a $H_2$ to HC molar ratio of between about 1 and about 5.

In general, the process of the invention is carried out in a fixed bed reactor containing the catalyst system described above. In a preferred embodiment, the first and second components of the catalyst system are in sequential beds in a single reactor. That is, the component of the catalyst system used in the process of the invention which is effective for ethylbenzene conversion forms a first bed, while the other component of the catalyst system, which is effective for xylene isomerization, forms a second bed downstream of the first bed. The feed is preferably cascaded from the first to the second bed without intervening separation of light gases. As an alternative, the first and second beds could be disposed in separate reactors which, if desired, could be operated at different process conditions. Additional catalyst beds may be provided prior or after the first and second catalyst components of the invention.

After the conversion process, the isomeration product can be treated to isolate paraxylene and/or other desirable xylene(s). Thus, for example, the isomerate product can be fed to a variety of paraxylene recovery units, such as a crystalizer, a membrane separation unit, or a selective adsorption unit (e.g., Parex™ unit), and thus the paraxylene may be isolated and recovered, leaving a paraxylene depleted C8 aromatic hydrocarbon by-product or residual isomerate. The residual isomerate can be stripped of products lighter than C8 aromatic hydrocarbons. Products heavier than C8 aromatic hydrocarbons in the residual isomerate can be further processed or may be fractionated out. C8 aromatic hydrocarbon fractions from which para-xylene has been removed can be recycled to the process.

The success of this method has been demonstrated in both pilot plant and commercial units. The start-up exotherms were successfully minimized, which led to improved catalyst performance. The following examples are meant to be illustrative of the present invention and not a limitation thereon. One of ordinary skill in the art in possession of the present disclosure will recognize that the invention may be practiced other than as specifically illustrated herein below.

EXAMPLE 1

The experiments were carried out in a pilot plant scale fixed bed unit. The reactor has a catalyst basket with 0.64" ID and 17.5" length. The basket was loaded with xylene isomerization catalyst extrudates. The top bed is $\frac{1}{20}$" quadrolobe shaped extrudates which contain Re supported on said solid extrudates composed of ZSM-5 molecular sieve and a binder. The bottom bed is $\frac{1}{16}$" cylindrical extrudates which contain Re on said solid extrudates composed of ZSM-5 molecular sieve and a binder. The dual-bed catalysts were packed in the reactor basket with a 35/65 bed ratio, by weight (first catalyst: second catalyst). The total fresh catalyst loading was 15.5 g. The reactor voids were filled with inert glass beads, and 80/120 mesh quartz sand was used to fill catalyst bed interstitial spaces. These measures were taken to minimize channeling of the reactant gas flow. The reactor is equipped with a thermal well ($\frac{1}{8}$"OD), to allow a traveling thermocouple to record the catalyst temperature along the bed axis, so that an average reactor temperature (ART) can be obtained.

The feedstock was commercial grade para-depleted mixed xylenes, which contained 16.2 wt % ethylbenzene, 1.9 wt % p-xylene, 15.3 wt % o-xylene, 64.7 wt % m-xylene, and 1.2 wt % toluene.

The catalysts were activated with temperature programmed reduction under hydrogen flow, followed by a metal passivation step via sulfiding.

When the catalyst was pre-sulfided, the reactor bed was held at the final reduction temperature (365° C.) before introducing $H_2S$ stream. A sulfur containing gas mixture ($H_2$ and $H_2S$) was used in the sulfiding process. The $H_2S$ concentration in the gas mixture was 400 vppm. The sulfiding gas flowrate and sulfiding time were set to give 1.9-fold coverage of rhenium atoms stoichiometrically (the chemisorption assumed to form $ReS_2$ compound). $H_2S$ breakthrough (>100 vppm $H_2S$) was detected at the reactor outlet by a Draeger tube.

The unit was subsequently started-up with feed introduction at a low weight hourly space velocity (WHSV) of 5.4 $hr^{-1}$, which is about 20-50% of design capability and high hydrogen to hydrocarbon molar ratio ($H_2$/HC) of 9:1, simulating commercial unit startup conditions. The feed rate was increased gradually while $H_2$/HC was decreased.

Figure 2:
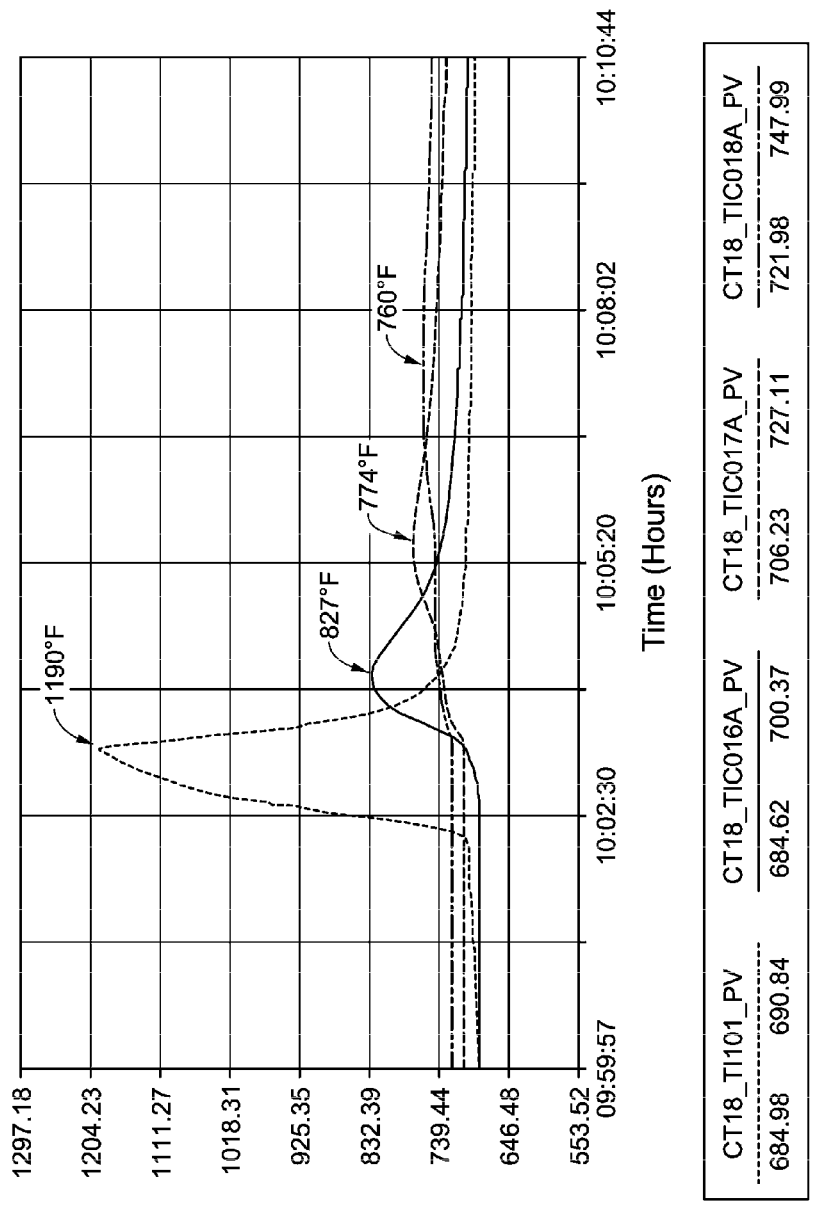
FIG. 2 is a temperature profile of the catalyst bed showing a large start-up exotherm using a freshly reduced catalyst.

FIG. 1 shows the catalyst temperature profiles at multiple points along the bed length during the oil-in period. No exotherm was observed during the entire oil-in period. As a direct comparison, when the catalyst was not sulfided, and otherwise under the same conditions, the initial feed introduction resulted in a large exotherm, as shown in FIG. 2.

Figure 3:
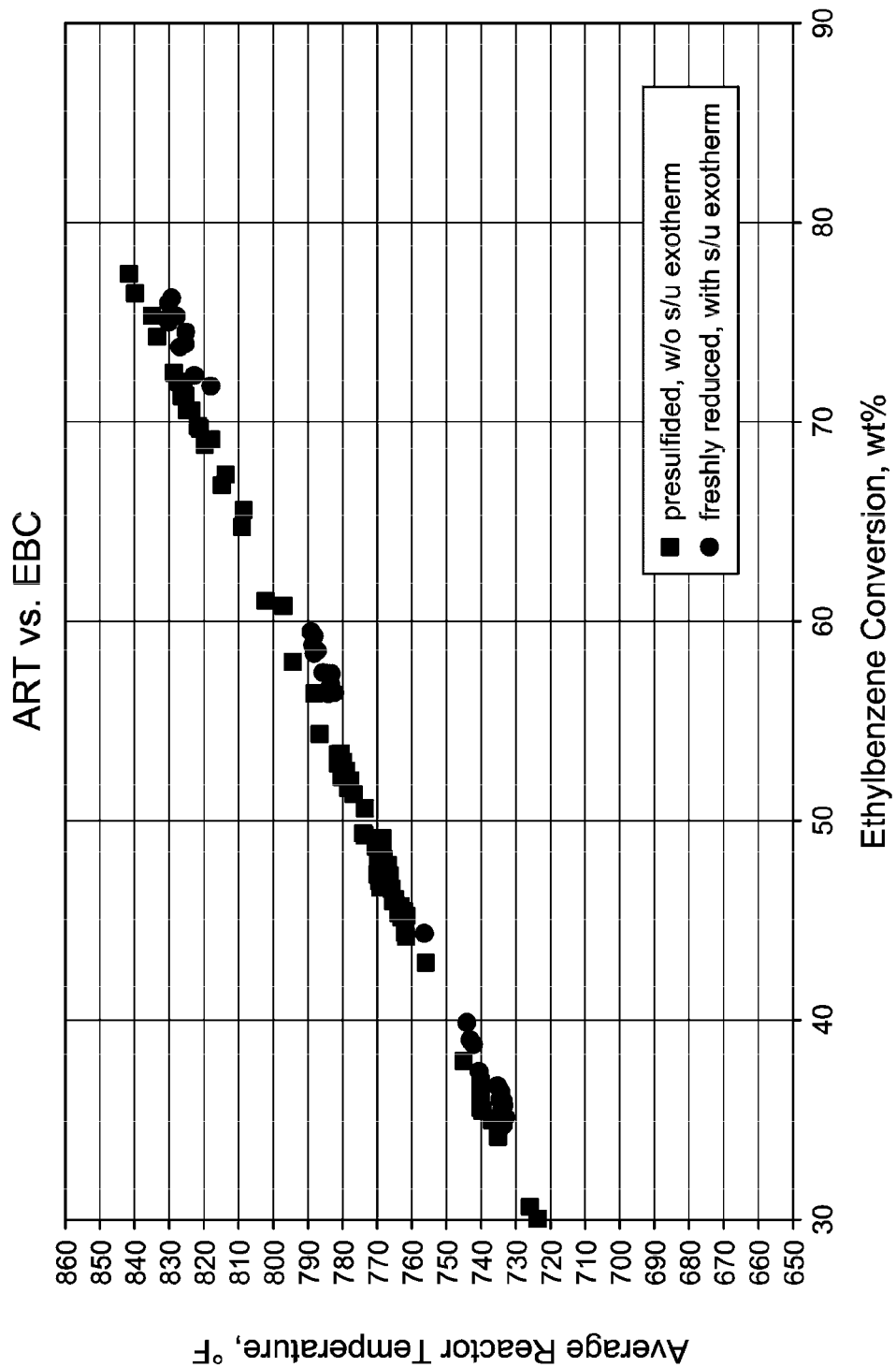
FIG. 3 shows a performance comparison between the presulfided catalyst and the freshly reduced catalyst with respect to dealkylation activity.

FIGS. 3, 4 and 5 show the performance comparison between the presulfided catalyst according to the present invention and the freshly reduced non-presulfided catalyst. The presulfided catalyst showed comparable ethyl benzene (EB) dealkylation activity (FIG. 3), higher paraxylene approach to equilibrium (PXAE) (FIG. 4), and comparable or slightly lower xylene loss (FIG. 5). In addition, an approximately 30-day aging test demonstrated that the presulfided catalyst showed the same aging rate as that of non-sulfided catalyst. This verified that the presulfiding did not create any negative impact on the catalyst long-term performance.

EXAMPLE 2

In commercial unit A, the presulfiding method according to the invention was implemented. The sulfiding agent used was dimethyl-disulfide (DMDS) liquid. The injection facilities consisted of a storage barrel of DMDS on a weight scale, two positive displacement pumps, and associated stainless steel tubing. Pre-sulfiding of the fresh xylene isomerization catalyst started immediately following completion of the catalyst dry-out. The catalyst bed was maintained at an elevated temperature of 359° C.

DMDS decomposed to $H_2S$ and $CH_4$ once it was injected into the reactor. The DMDS injection rates were set to give 500 vppm (sometime termed ppmV, or parts per million by volume) $H_2S$ at the reactor inlet. The recycle gas was monitored for $H_2S$ breakthrough via Draeger tubes. The total sulfur injected corresponded to 1 equivalent of catalyst metal content. Breakthrough of $H_2S$ (>100 vppm in recycle gas) was detected during this commercial catalyst presulfiding application. No temperature rise was detected in the reactor during DMDS injection.

Oil-in began immediately following pre-sulfiding. The initial feed rate was at 65% of design, and the initial $H_2$/HC ratio was approximately 1.8:1. The wetting exotherm was very mild compared to previous fresh catalyst start-ups. The exotherm (maximum bed T–inlet T) was 10-17° C., with an observed maximum bed temperature of 371° C. This compares to the maximum temperatures during previous start-ups of 590-700° C., when the catalyst was not sulfided.

Table 1 shows the performance comparison between the presulfided catalyst and the non-sulfided catalyst with start-up exotherm at similar operating conditions and time-on-stream. The presulfided catalyst showed much higher EB dealkylation activity as measured by the normalized average reactor temperature (NART), higher paraxylene approach to equilibrium (PXAE), and comparable xylene loss.

TABLE 1

Commercial Unit A performance comparison between the presulfided catalyst and the freshly reduced catalyst.

| Catalyst | Normalized Average Reactor Temperature*, ° C. | ParaXylene Approach Equilibrium, % | Xylene Loss, % |
|---|---|---|---|
| Presulfided, No startup exotherm | 410 | 103.9 | 1.6 |
| Freshly reduced, Large startup exotherm | 462 | 100.1 | 1.6 |

*Normalized to 15 WHSV, 1.7$H_2$/HC, 55% EBC (Ethyl Benzene Conversion)

EXAMPLE 3

Commercial Unit B

In commercial unit B, independent DMDS injection facilities were used to introduce sulfur to two parallel reactors simultaneously as soon as the catalyst dry-out and reduction processes were completed. The presulfiding was conducted at the reactor temperature of 360° C., and the inlet pressure of 1.3 MPa. The DMDS injection rates were set to give 500 vppm $H_2S$ concentration at the reactor inlet. Recycle gas $H_2S$ concentration was monitored frequently during the presulfiding process. Hydrocarbon feed introduction started immediately after the 2× sulfur equivalents (based on metal atom content) were injected. No $H_2S$ breakthrough was detected in the recycle gas. Without wishing to be bound by theory, it is believed that the large metal surface area of the reactors and the feed/effluent heat exchangers had adsorped additional sulfur.

The initial feed rate was at 28% of the design. Low WHSV relative to design gives high $H_2$/HC at constant recycle gas rate. Both typically will lead to more exotherm. The $H_2$/HC ratio was at approximately 6. A very small wetting exotherm (<5° C.) was observed following oil-in. This compares to large reactor bed temperature increases of 120-135° C. during previous start-ups.

Table 2 shows the performance comparison between the presulfided catalyst and the non-sulfided catalyst with start-up exotherm. The presulfided catalyst showed higher EB dealkylation activity (low NART), much higher p-xylene approach equilibrium (PXAE), and comparable or lower xylene loss.

TABLE 2

Commercial Unit B performance comparison between the presulfided catalyst and the freshly reduced catalyst.

| Catalyst | Normalized Average Reactor Temperature*, ° C. | ParaXylene Approach Equilibrium, % | Xylene Loss, % |
|---|---|---|---|
| Presulfided, No startup exotherm | 395 | 101.0 | 0.65 |
| Freshly reduced, Large startup exotherm | 405 | 93.0 | 0.73 |

*Normalized to 18 WHSV, 1.5$H_2$/HC, 40% EBC

In light of the above description and having provided numerous details including preferred embodiments and specific example, it will be understood that various other modifications will be apparent to and can be readily made by those skilled in the art without departing from the spirit and scope of the invention.

Trade names used herein are indicated by a ™ symbol or ® symbol, indicating that the names may be protected by certain trademark rights, e.g., they may be registered trademarks in various jurisdictions. All patents and patent applications, test procedures (such as ASTM methods, UL methods, and the like), and other documents cited herein are fully incorporated by reference to the extent such disclosure is not inconsistent with this invention and for all jurisdictions in which such incorporation is permitted. When numerical lower limits and numerical upper limits are listed herein, ranges from any lower limit to any upper limit are contemplated.

What is claimed is:

1. A process for preparing paraxylene comprising:
   (a) contacting a C8 aromatic hydrocarbon mixture including ethylbenzene and at least one xylene isomer other than paraxylene, in the presence of hydrogen and under suitable ethylbenzene de-alkylating conditions, with at least a first catalyst having an average crystal size of greater than 1 micron and comprising at least a first hydrogenation component, said component supported on a molecular sieve, wherein said catalyst is suitable for de-alkylation of ethylbenzene and further characterized as having been subjected to a sulfiding treatment prior to said contacting, to produce a ethylbenzene-depleted aromatic hydrocarbon mixture; then
   (b) contacting said ethylbenzene-depleted C8 aromatic hydrocarbon mixture, in the presence of hydrogen and under suitable xylene isomerization conditions, with at least a second catalyst having an average crystal size of 0.02 to 0.05 microns and comprising at least a second hydrogenation component, said component supported on a molecular sieve, wherein said catalyst is suitable for xylene isomerization and further characterized as having been subjected to a sulfiding treatment prior to said contacting, to produce a paraxylene-enriched C8 aromatic hydrocarbon mixture, when compared with said C8 aromatic hydrocarbon mixture of step (a),
   wherein each of said molecular sieves of the first and second catalysts is independently selected from the group consisting of ZSM-5, ZSM-11, ZSM-12, ZSM-22, ZSM-23, ZSM-35, ZSM-38, ZSM-48, ZSM-57, ZSM-58, and mixtures thereof, wherein said first catalyst has a higher alpha value than said second catalyst, wherein at least one of the first and second catalysts is not silica selectivated and wherein said first and second hydrogenation components are each independently selected from Groups 6-11 and 14-15 of the Periodic Table.

2. The process of claim 1, wherein said sulfiding treatment in at least one of steps (a) and (b) is carried out in a hydrogen sulfide current at a temperature of 100° to 450° C.

3. The process of claim 1, wherein at least one of said first and second catalysts is steam-treated prior to said sulfiding treatment.

4. The process of claim 1, wherein at least one of said first and second catalysts comprises a hydrogenation component in the reduced state prior to said sulfiding.

5. The process of claim 1, wherein at least one of said first and second catalysts is/are sulfided by exposure to hydrogen sulfide at a temperature of from above room temperature to 540° C. for a period of time sufficient to provide sulfur in an amount of at least 0.5 equivalents based on the catalyst metal content.

6. The process of claim 1, wherein said at least one first catalyst is in a first bed and said at least one second catalyst is in a second bed and wherein said ethylbenzene-depleted aromatic hydrocarbon mixture is cascaded from the first bed to said second bed without intervening separation of light gases.

7. The process of claim 1, wherein said at least one first catalyst has a crystal size of greater than 1 micron and said at least one second catalyst has a crystal size of from 0.02 to 0.05 microns.

8. The process of claim 1, wherein said first and second hydrogenation compounds are rhenium.

* * * * *